(12) United States Patent
Baschnagel (10) Patent No.: US 8,283,514 B2
(45) Date of Patent: Oct. 9, 2012

(54) ADHESIVE BANDAGE

(76) Inventor: Robert J. Baschnagel, Garden City, NY (US)

( * ) Notice: Subject to any disclaimer, the term of this patent is extended or adjusted under 35 U.S.C. 154(b) by 422 days.

(21) Appl. No.: 12/582,866

(22) Filed: Oct. 21, 2009

(65) Prior Publication Data

US 2011/0092874 A1    Apr. 21, 2011

(51) Int. Cl.
*A61F 5/00* (2006.01)
*A61F 13/00* (2006.01)
*A61L 15/16* (2006.01)

(52) U.S. Cl. ........... 602/54; 424/443; 424/446; 604/306

(58) Field of Classification Search .......... 604/306–307; 602/41–43, 54, 56, 48; 424/443–449
See application file for complete search history.

(56) References Cited

U.S. PATENT DOCUMENTS

| | | | |
|---|---|---|---|
| 4,117,841 A | 10/1978 | Perrotta et al. | |
| 4,689,044 A * | 8/1987 | Murata | 604/306 |
| 5,086,763 A * | 2/1992 | Hathman | 602/42 |
| 2008/0167633 A1 | 7/2008 | Vannucci | |

OTHER PUBLICATIONS

International Search Report and Written Opinion dated Jun. 23, 2011.

* cited by examiner

*Primary Examiner* — Patricia Bianco
*Assistant Examiner* — Ophelia Hawthorne
(74) *Attorney, Agent, or Firm* — Scully, Scott, Murphy & Presser, P.C.

(57) ABSTRACT

An adhesive bandage is provided with a body portion having a gauze portion and an adhesive portion. The adhesive portion having an adhesive on a first surface of the body portion adapted to adhere to skin. The body portion having a cavity for storing two or more gauze portions, the cavity having a first opening on the first surface for exposing one of the two or more gauze portions to the skin and a second opening on a second surface for removing the exposed gauze portion through the second opening and replacing the exposed gauze portion with another of the two or more gauze portions in the first opening. Also provided are adhesive bandages having a cavity for storing a medicament or a port, each in communication with the gauze portion for providing medicament to the gauze portion.

16 Claims, 14 Drawing Sheets

ADHESIVE BANDAGE

BACKGROUND

1. Field

The present invention relates generally to bandages and, more particularly, to adhesive bandages.

2. Prior Art

Adhesive bandages are well known in the art. Such bandages typically have a pair of adhesive portions on each side of a gauze pad. The gauze pad is positioned on an affected area of the skin, such as a scrape or cut and the adhesive portions hold the gauze pad in place. However, the gauze portion of the adhesive bandage is often easily soiled with medicaments and/or bodily fluids and must be replaced often. Furthermore, medicament often needs to be replenished in order to properly promote healing and prevent infection, which requires removal and replacement of the bandage each time the medicament is replenished. Lastly, the gauze pad is typically in contact with the affected area of the skin and tends to rub off any medicament on the affected area.

SUMMARY

Accordingly, an adhesive bandage is provided. The adhesive bandage comprises: a body portion having a gauze portion and an adhesive portion; the adhesive portion having an adhesive on a first surface of the body portion adapted to adhere to skin; and the body portion having a cavity for storing two or more gauze portions, the cavity having a first opening on the first surface for exposing one of the two or more gauze portions to the skin and a second opening on a second surface for removing the exposed gauze portion through the second opening and replacing the exposed gauze portion with another of the two or more gauze portions in the first opening.

The two or more gauze portions can be each separated by a separation portion allowing the exposed gauzed portion removed through the second opening to be separated from another of the two or more gauze portions.

The cavity can have a first portion and a second portion, the first portion having the first opening for storing the exposed gauze portion and the second portion for storing the other of the two or more gauze portions.

The separated portion can be a weakened portion, which is torn more easily than the gauze portion is torn.

The separated portion corresponding to the exposed gauze portion can be exposed through the second opening such that it can be pulled to remove the exposed gauze portion through the second opening and pull a subsequent one of the two or more gauze portions into the first opening.

The second opening can be a slit.

A method for changing a first gauze portion associated with an adhesive bandage is also provided. The method comprising: adhering the adhesive bandage to a skin of a patient with the first gauze portion corresponding to a injured portion of the skin; subsequent to the adhering, removing the first gauze portion; and replacing the first gauze portion with a second gauze portion over the injured portion of the skin while the adhesive bandage remains adhered to the skin.

The removing can comprise pulling the first gauze portion through an opening on the adhesive bandage.

The replacing can comprise attaching the first gauze portion to the second gauze portion such that pulling the first gauze portion through the opening causes the second gauze portion to be positioned over the injured portion of the skin.

Also provided is an adhesive bandage comprising: a body portion having a gauze portion and an adhesive portion; the adhesive portion having an adhesive on a surface of the body portion adapted to adhere to skin; the body portion having at least one cavity for storing a medicament, the at least one cavity having an opening in communication with the gauze portion such that an application of pressure to the at least one cavity causes the medicament to flow into the gauze portion.

The at least one cavity can comprise two cavities, each having an opening in communication with the gauze portion.

Still further provided is an adhesive bandage comprising: a body portion having a gauze portion and an adhesive portion; the adhesive portion having an adhesive on a first surface of the body portion adapted to adhere to skin; the body portion having a port in communication with the gauze portion for introducing a medicament to the gauze portion.

The port can be disposed on a second surface opposite to the first surface having the adhesive.

The port can be collapsible onto the second surface.

The port can be adhered to the second surface when in a collapsed state.

The port can be foldable into a shape having a reduced surface area when not being used.

The port can be unfoldable into a funnel shape when being used.

BRIEF DESCRIPTION OF THE DRAWINGS

These and other features, aspects, and advantages of the apparatus and methods of the present invention will become better understood with regard to the following description, appended claims, and accompanying drawings where:

DETAILED DESCRIPTION OF THE PREFERRED EMBODIMENT

Figure 1:
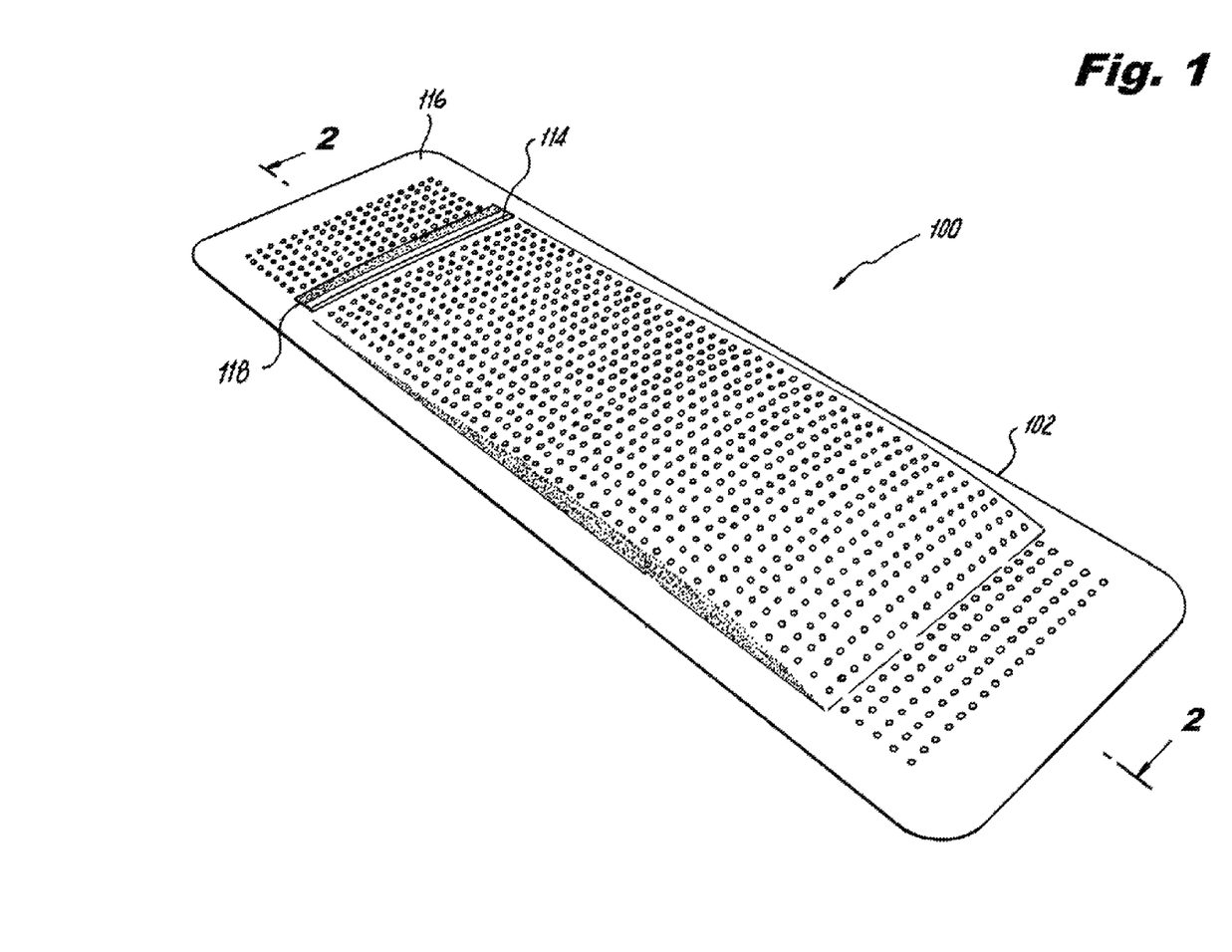
FIG. 1 illustrates a perspective view of an adhesive bandage according to a first embodiment.
Figure 2:
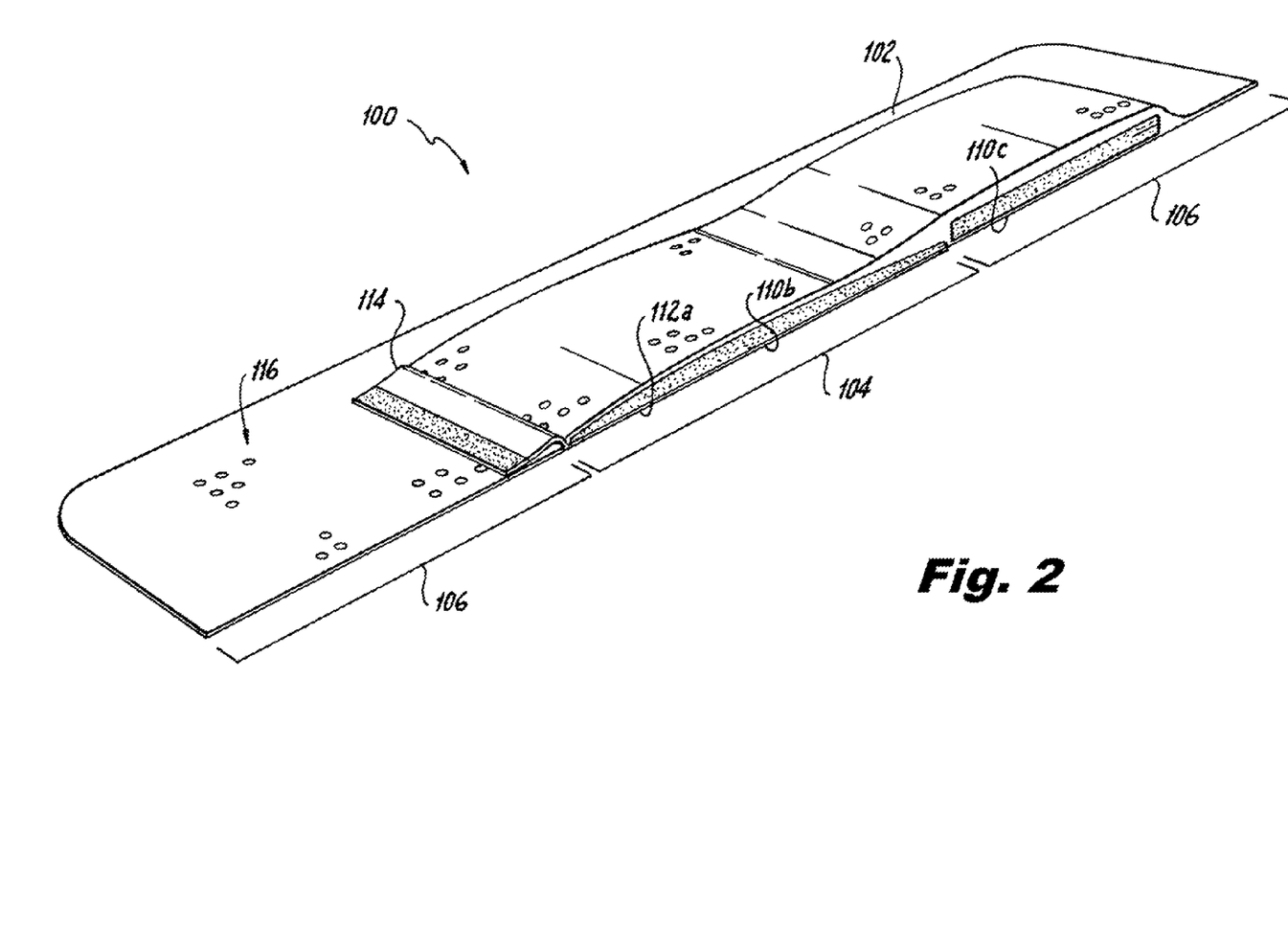
FIG. 2 illustrates a perspective cross-sectional view of the adhesive bandage of FIG. 1 as taken along sectional line 2-2 in FIG. 1.
Figure 3:
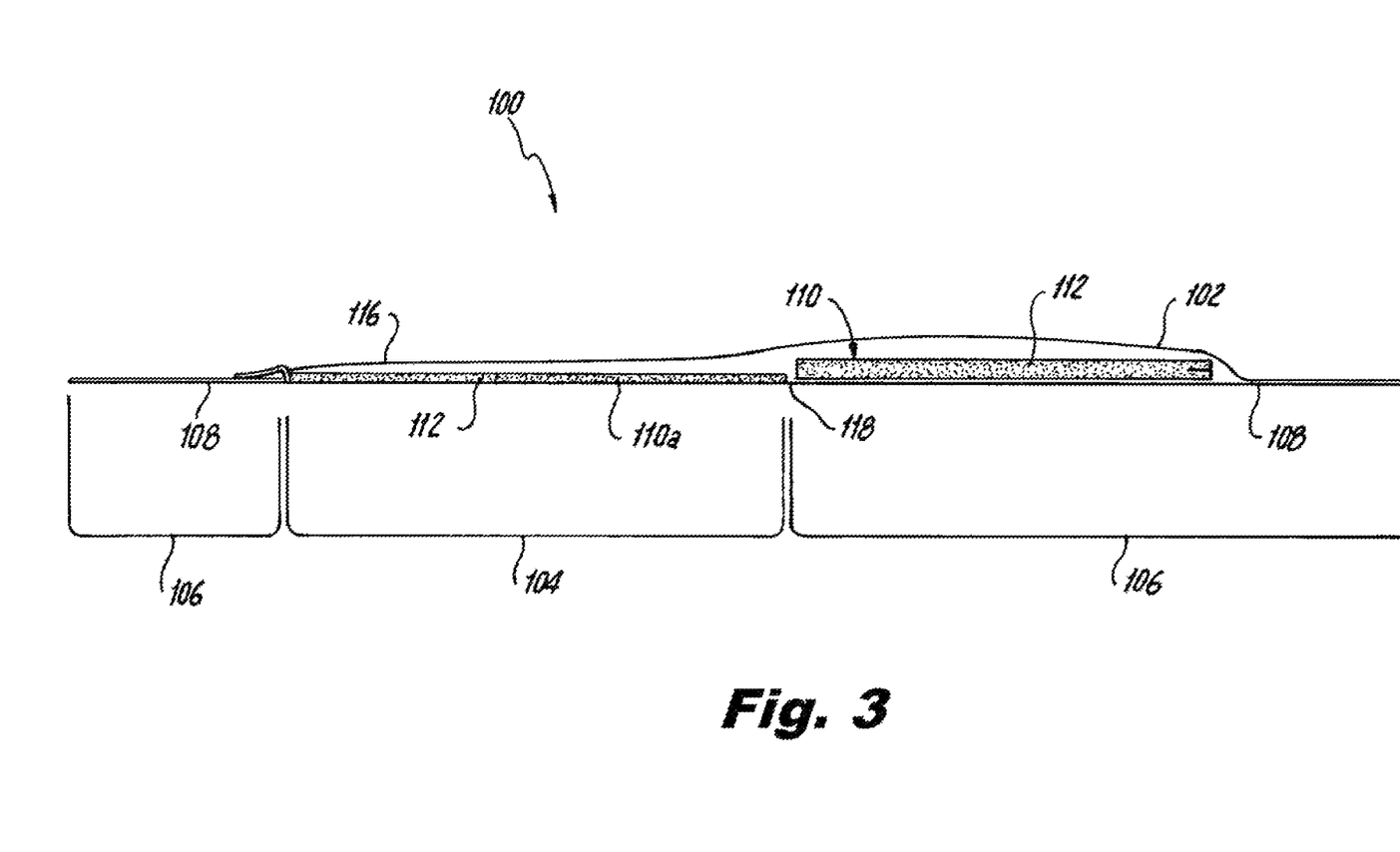
FIG. 3 illustrates a side view of the sectional view of FIG. 2.

Referring now to FIGS. 1-3, there is shown an adhesive bandage according to a first embodiment. The adhesive bandage being generally referred to by reference numeral 100. The adhesive bandage 100 having a body portion 102. The body portion 102 being formed of materials known in the art for use with adhesive bandages, such as a plastic film or fabric sheet. The body portion 102 having a gauze portion 104 and an adhesive portion 106. The gauze portion 104 being formed of a gauze material, such as cotton and being positioned so as to be in contact with an injured portion of the skin of a patient when the adhesive bandage 100 is applied over such injured portion. The adhesive portion 106 having an adhesive on a first surface 108 of the body portion 102 for adhering to portions of the skin adjacent to the injured portion, as is known in the art of adhesive bandages.

The body portion 102 further having a cavity 110 for storing two or more gauze portions 112, the cavity 110 having a first opening 110a on the first surface 108 for exposing one 112a (hereinafter the "exposed gauze portion") of the two or more gauze portions 112 to the skin and a second opening 114, such as a slit, on a second surface 116 for removing the exposed gauze portion 112a through the second opening 114 and replacing the exposed gauze portion 112a with another of the two or more gauze portions 112 in the first opening 110a. The cavity can have a first portion 110b and a second portion 110c where the first portion 110b has the first opening 110a for storing the exposed gauze portion 112a and the second portion 110c for storing the other of the two or more gauze portions 112.

The two or more gauze portions 112 can be each separated by a separation portion 118 (as seen clearly in FIG. 4e) which allows the exposed gauzed portion 112a to be removed through the second opening 114 and to be separated from another of the two or more gauze portions 112. The separated portion 118 can be cut with a scissors or other instrument to separate the exposed gauze portion 112a from the other of the two or more gauze portions 112 or have a weakened portion which can be torn more easily than the gauze portion is torn. For example, the weakened portion can be perforated.

Figure 4A:
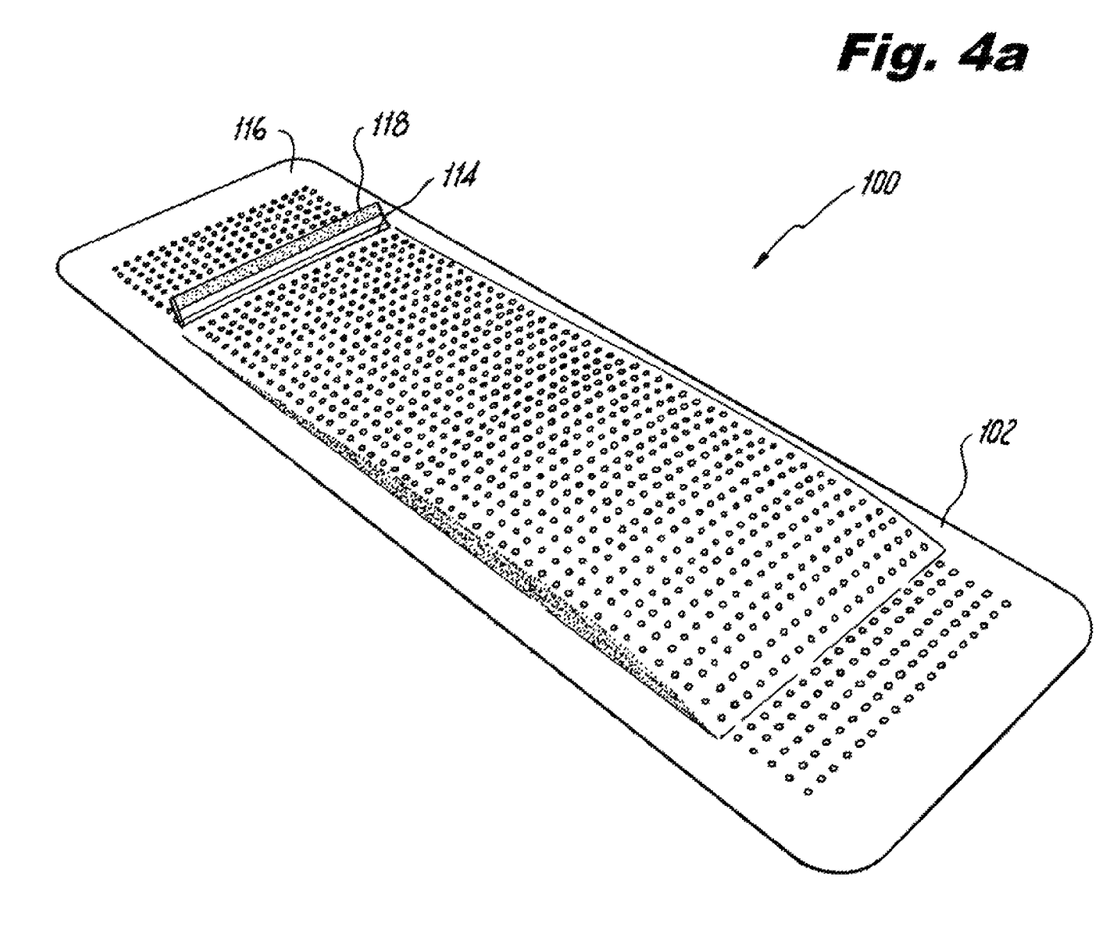
FIGS. 4a-4f illustrate a usage of the adhesive bandage of FIG. 1.

Referring now to FIGS. 4a-4f, the use of the adhesive bandage 100 according to the first embodiment will be described. FIG. 4a illustrates the adhesive bandage 100 with the exposed gauze portion 112a exposed through the first opening 110a, such that the adhesive bandage 100 can be applied over an injured portion of the skin with the exposed gauze portion 112a corresponding to the injured portion and the adhesive portion 106 being applied and adhered to skin adjacent to the injured portion. FIG. 4a also shows an end of a separated portion 118 being exposed through the second opening 114.

Figure 4B:
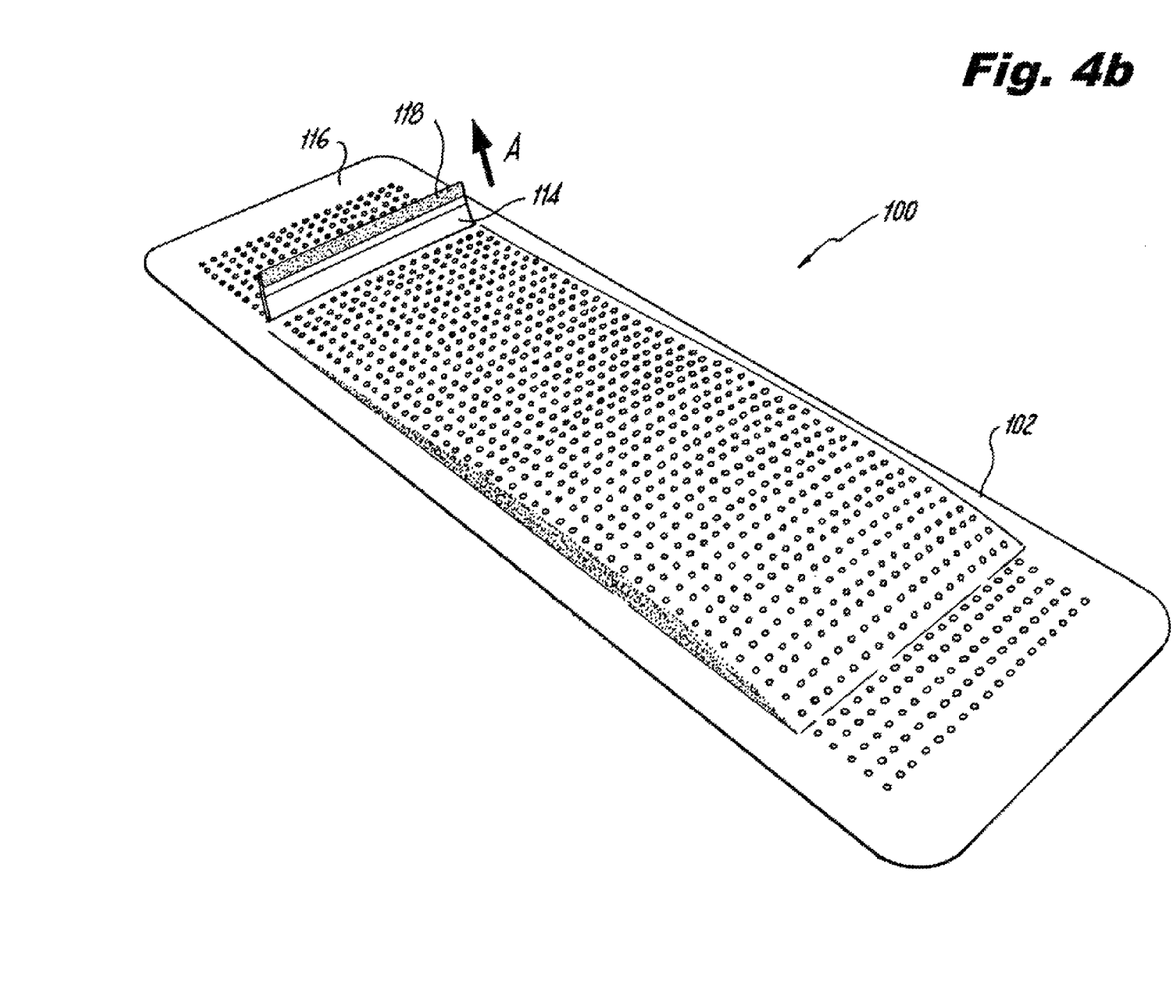
Figure 4C:
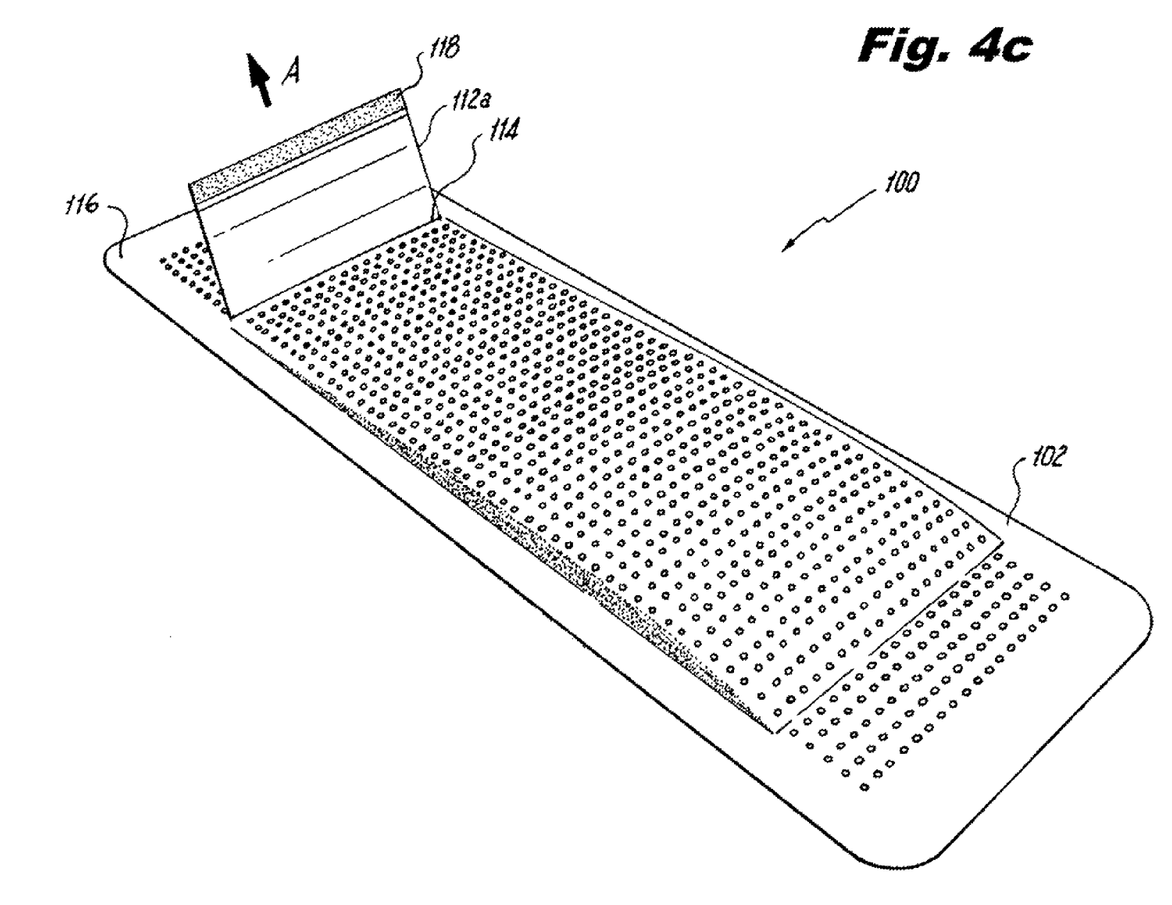
Figure 4D:
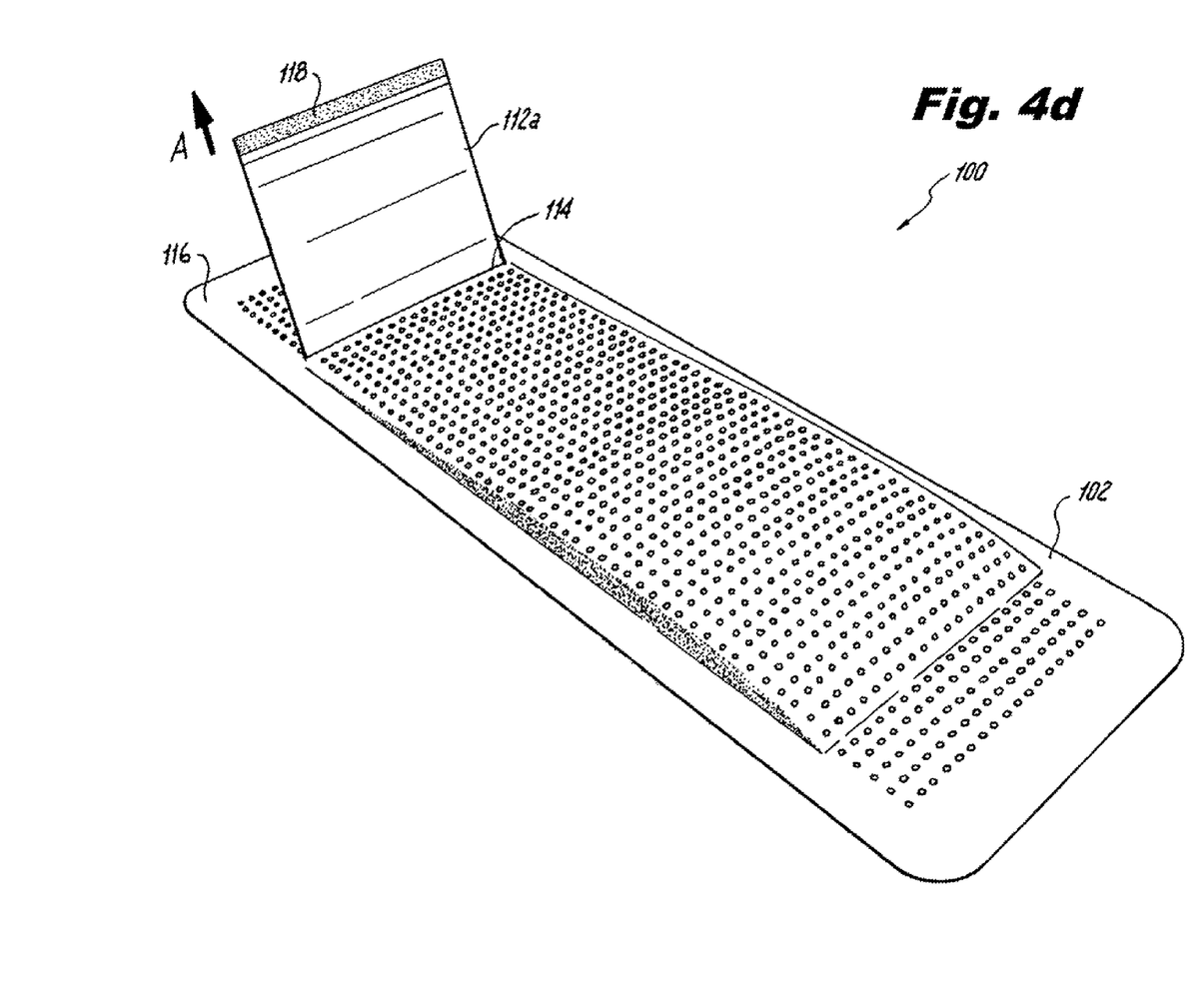
Figure 4E:
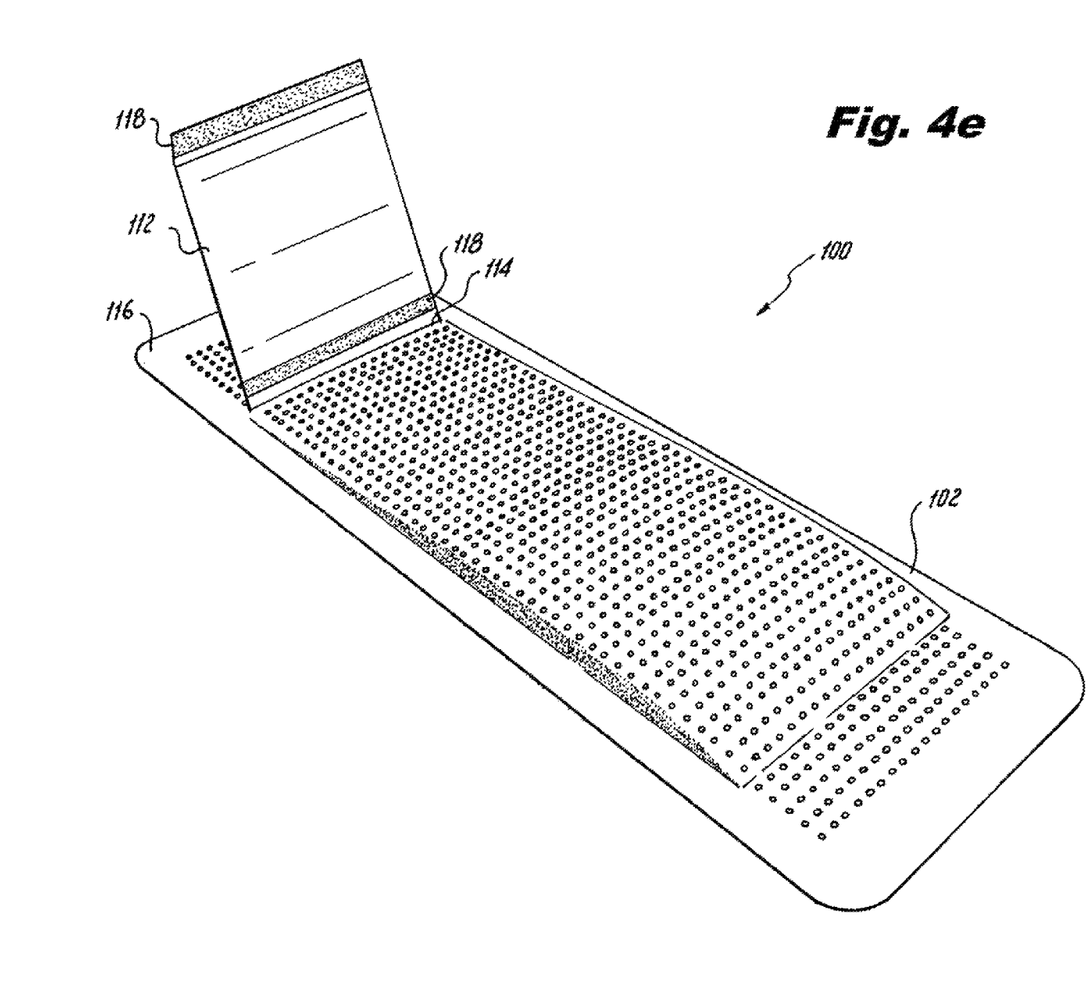

FIGS. 4b, 4c and 4d illustrate various stages of the end of the separated portion being lifted and pulled in the direction of arrow A. Referring now to FIG. 4e in combination with FIG. 3, the separated portion is continued to be pulled to the point where the next separated portion 118a is exposed through the second opening 114. At this point, the exposed gauze portion 112a is completely removed through the second opening 114. Referring to FIG. 3 in combination with FIG. 4e, a subsequent one of the two or more gauze portions 112 is pulled into the first opening 110a to be the exposed gauze portion 112a.

Thus, the adhesive bandage 100 is first adhered to the skin of a patient with the exposed gauze portion 112a corresponding to the injured portion of the skin. Subsequent to the adhering of the adhesive bandage, the exposed gauze portion 112a is pulled through the second opening 114 to replace the exposed gauze portion 112a with one of the two or more gauze portions 112 that were previously stored in the second cavity 110c. Thus, the new exposed gauze portion is positioned to correspond with the injured portion of the skin while the adhesive bandage remains adhered to the skin. Therefore, a fresh gauze portion can be replaced over the injured portion of the skin without removing the adhesive bandage 100 from the skin.

Figure 4F:
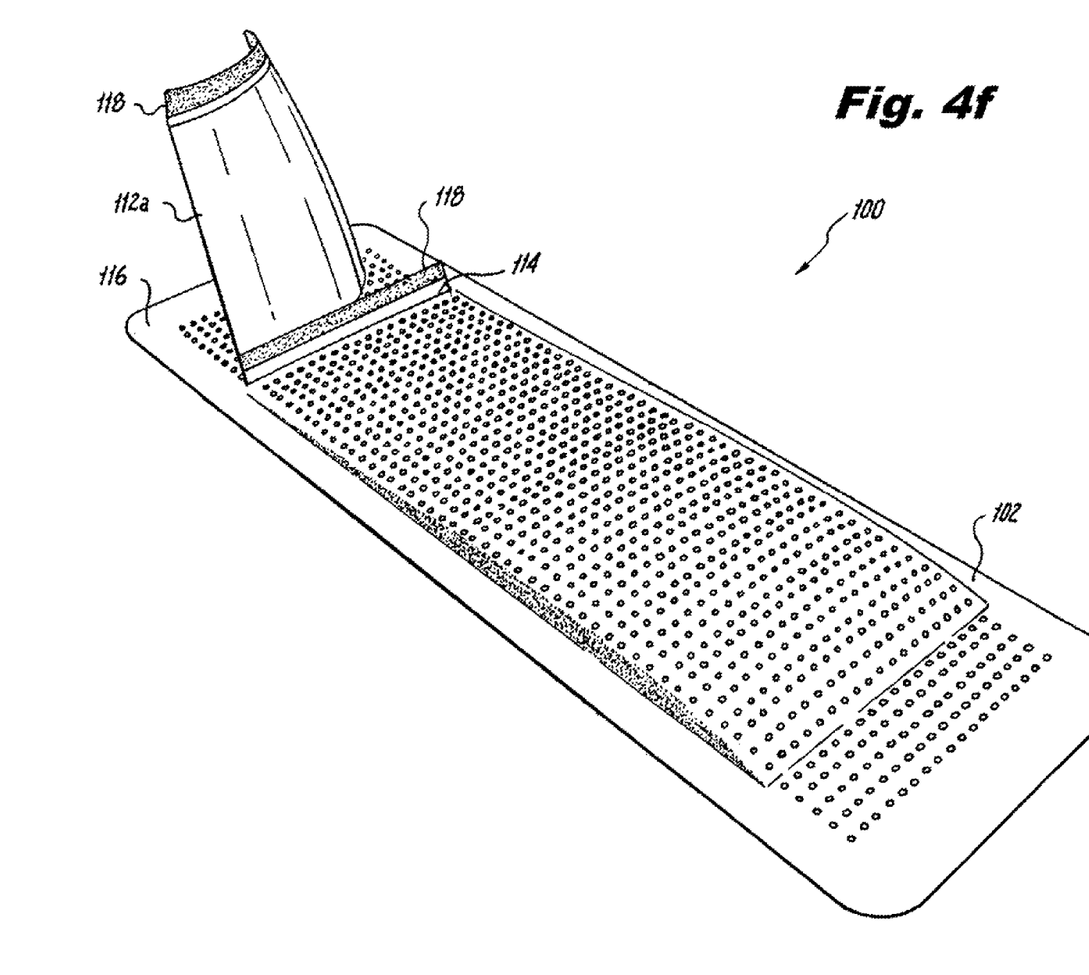

Referring now to FIG. 4f, the previous exposed portion 112a that has been removed through the second opening 114, can be removed, such as by cutting or tearing and discarded. Such procedure can be repeated as often as necessary to maintain a fresh gauze portion over the injured portion of the skin until all of the gauze portions in the first and second cavities 110b, 110c are exhausted.

Figure 5:
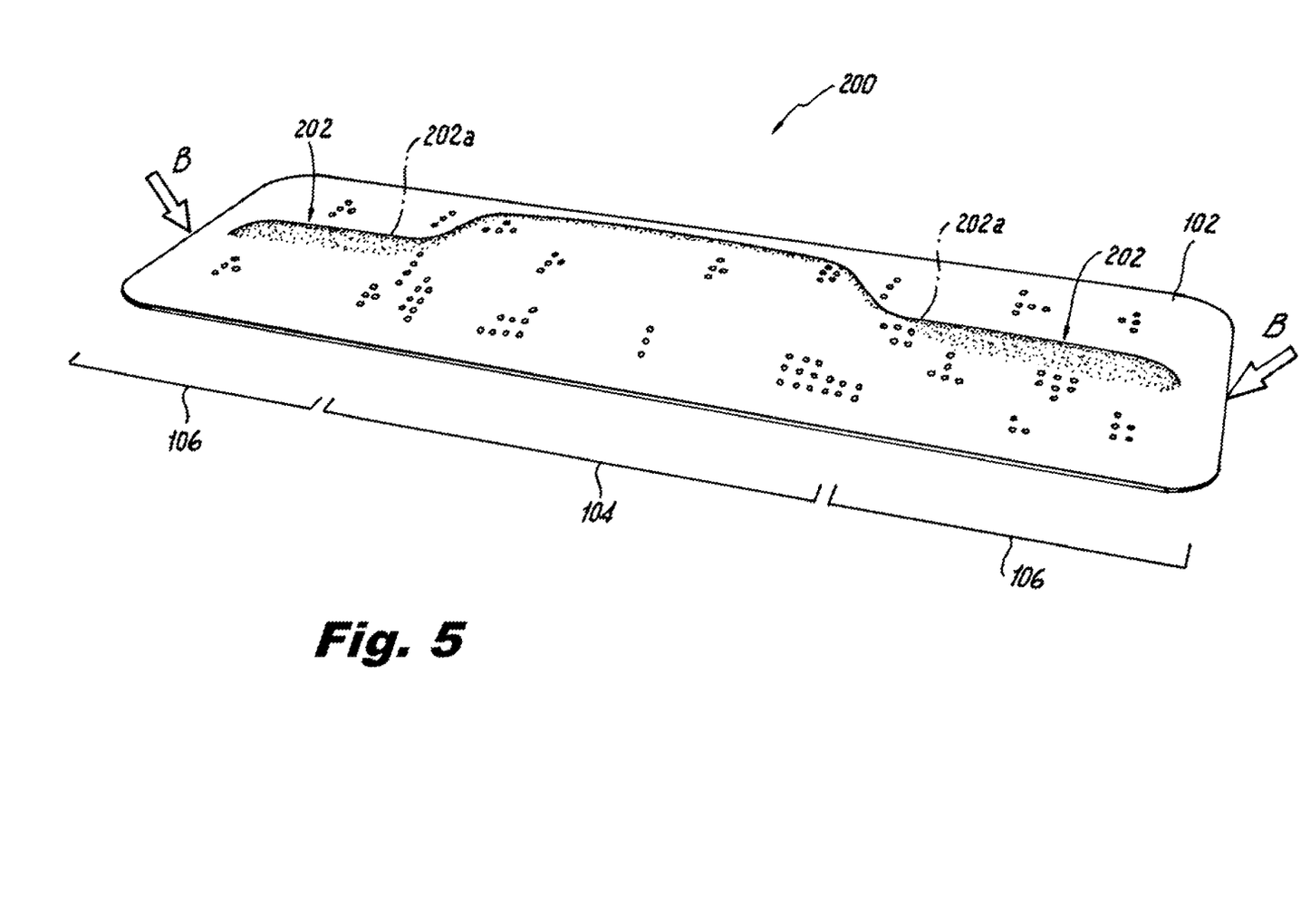
FIG. 5 illustrates a perspective view of an adhesive bandage according to a second embodiment.

Referring now to FIG. 5, there is shown an adhesive bandage according to a second embodiment. The adhesive bandage of FIG. 5 being generally referred to by reference numeral 200. The adhesive bandage 200 having a body portion 102, which includes a gauze portion 104, and an adhesive portion 106 as was described generally with regard to the embodiment of FIG. 1, the same reference numerals denoting similar features. As with the adhesive bandage 100 of the embodiment of FIG. 1, the adhesive portion 106 of adhesive bandage 200 has an adhesive on a first surface 108 of the body portion 102, which is adapted to adhere to skin.

The body portion 102 has at least one cavity 202 for storing a medicament. Although two such cavities are shown in FIG. 5, less or more are possible. The at least one cavity 202 can be a void formed in the body portion 102 or a capsule embedded therein. Such capsules are well known in the art and are generally formed of thin walled plastic that is easily deformed by squeezing and having a narrowed portion in which an opening is formed. The opening 202a of each of the at least one cavities 202 are in communication with the gauze portion 104 such that an application of pressure to the at least one cavity 202 causes the medicament to flow into the gauze portion 104. The medicament can be any liquid or gel that has some therapeutic value to the injured portion of the skin. The opening 202a can also be closed and be formed so as to burst open upon the application of a predetermined amount of pressure to the cavities 202. The opening 202a can also have a valve that opens upon the application of the predetermined pressure, such as a duckbill or flap valve.

In general, the medicament can be applied to the gauze portion by the application of pressure with the fingers in the direction of arrows B in FIG. 5 and continuing towards the gauze portion 104. In this way, all of the medicament from the cavities 202 can be applied to the gauze portion 104 after the adhesive bandage 200 is already adhered to the skin, thus avoiding the mess of applying the medicament before application of the adhesive bandage and ensuring that the medicament is applied to the gauze portion and not to unintended portions, such as uninjured portions of the skin or to the adhesive portion 106. Alternatively, less than all of the medicament in the cavities 202 can be applied to the gauze portion 104, with the remaining portions being applied over time. As another alternative, the embodiments of FIGS. 1 and 5 can be combined such that the medicament can be applied each time a new exposed gauze portion 112a is pulled to the first opening 110a.

Referring now to FIGS. 6-9, there is shown an adhesive bandage according to a third embodiment. The adhesive bandage of FIGS. 6-9 being generally referred to by reference numeral 300. The adhesive bandage 300 has a body portion 102, which includes a gauze portion 104, and an adhesive portion 106 as was described generally with regard to the embodiment of FIG. 1, the same reference numerals denoting similar features. As with the adhesive bandage 100 of the embodiment of FIG. 1, the adhesive portion 106 of the adhesive bandage 300 has an adhesive on a first surface 108 of the body portion 102 adapted to adhere to skin.

Figure 6:
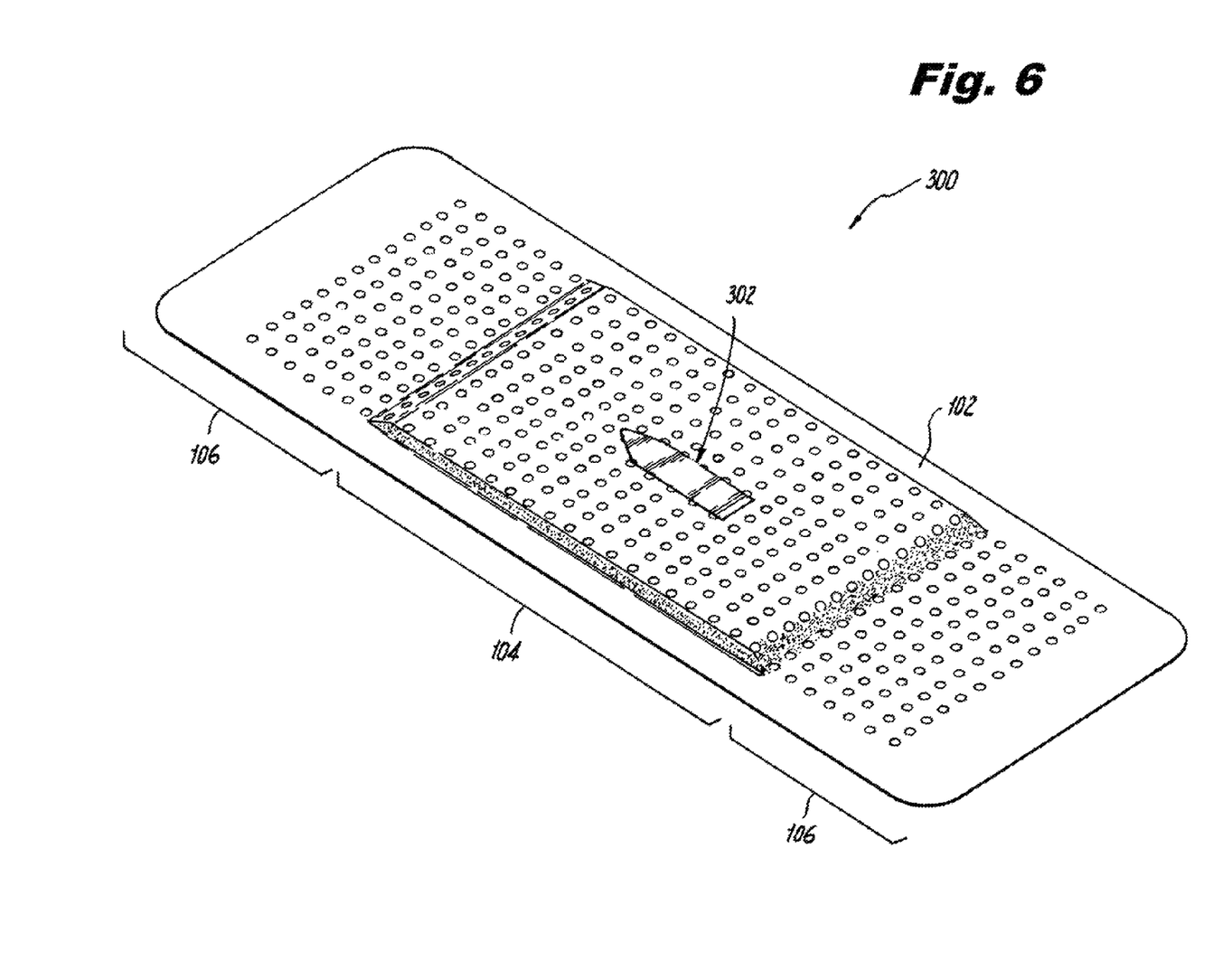
FIG. 6 illustrates a perspective view of an adhesive bandage according to a second embodiment.

The body portion 102 includes a port 302 in communication with the gauze portion 104 for introducing a medicament to the gauze portion 104. The port 302 is disposed on the second surface 116 opposite to the first surface 108 having the adhesive.

As shown in FIG. 6, the port 302 can be collapsible onto the second surface 116. As such, the port 302 can be adhered to the second surface with a releasable adhesive or merely lie on the second surface 116.

Figure 7:
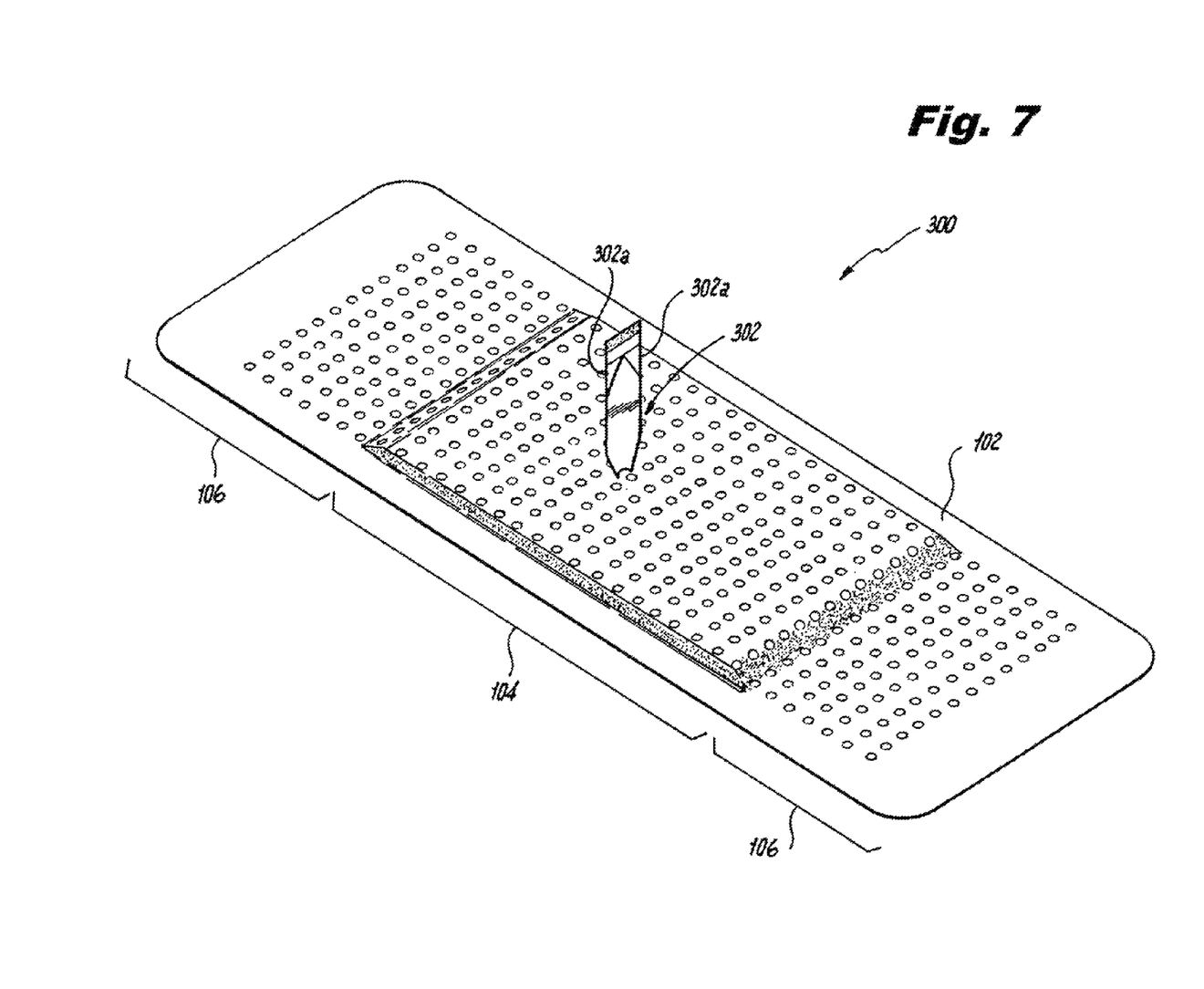
FIGS. 7-9 illustrate a usage of the adhesive bandage of FIG. 6.
Figure 8:
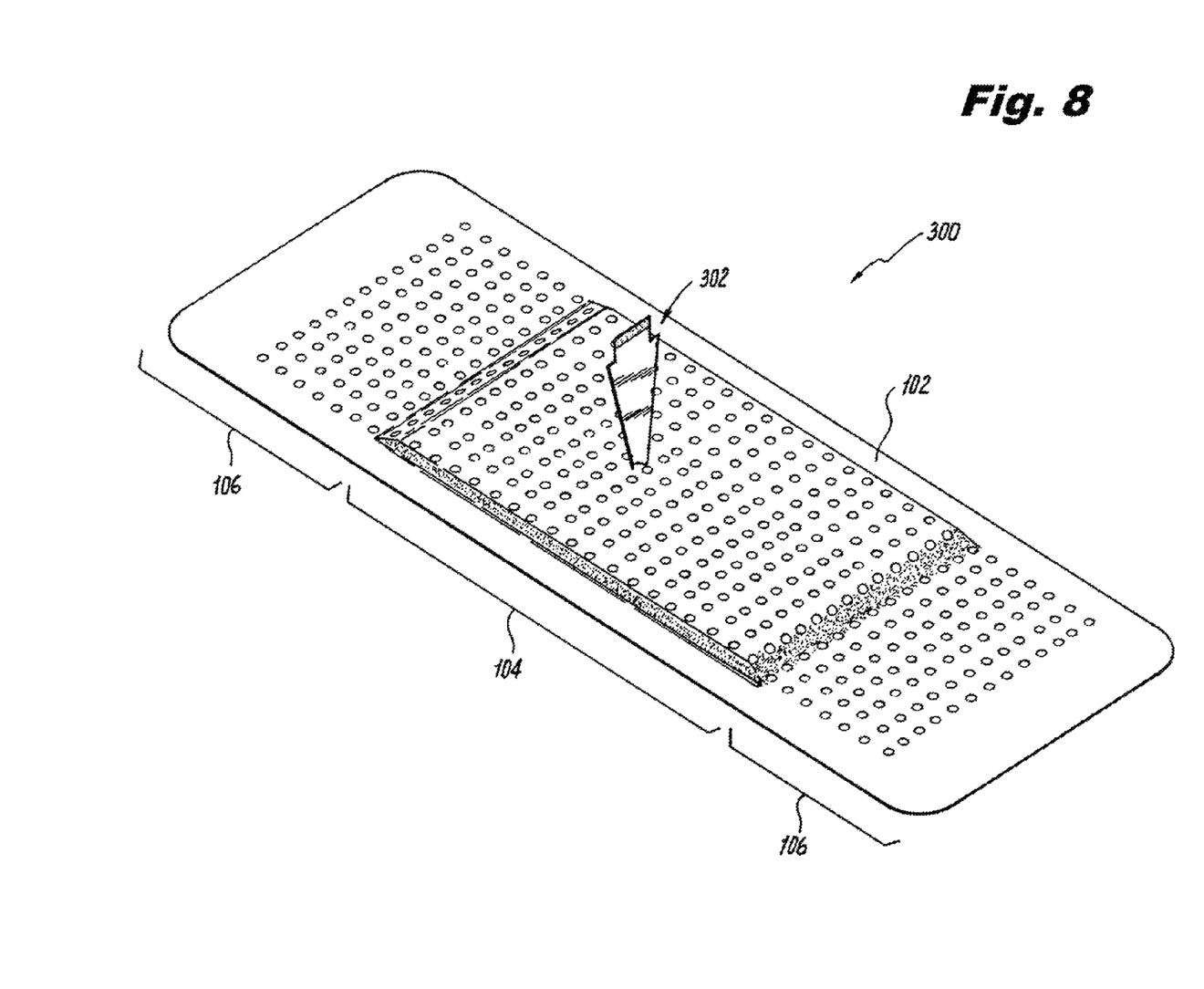
Figure 9:
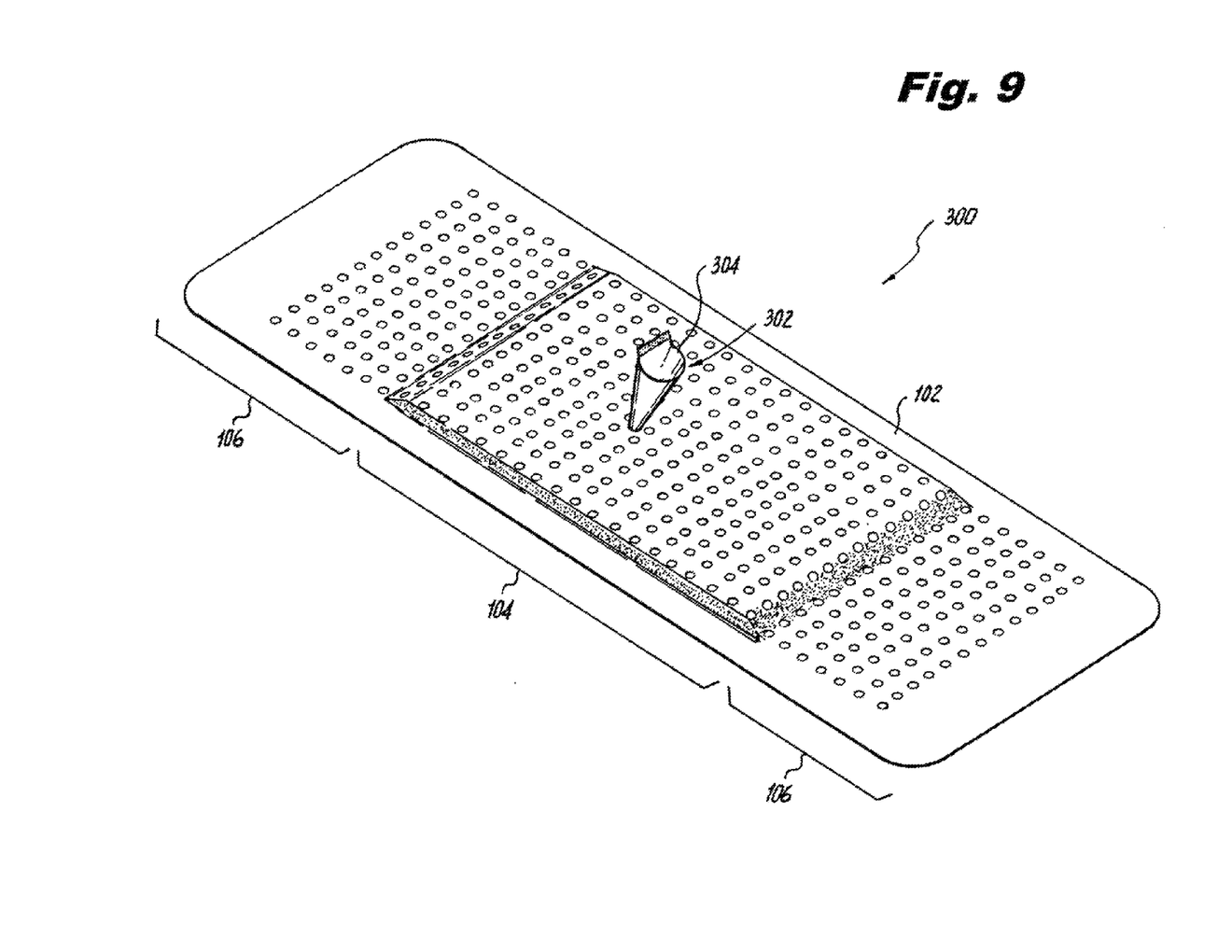

As shown in FIG. 7, the port 302 can also be foldable into a shape having a reduced surface area when not being used. FIG. 7 shows the port having folded portions 302a, which can be unfolded as shown in FIG. 8 after the port 302 is lifted from the second surface 116. As shown in FIG. 9, after being lifted and unfolded, the port 302 can be opened into a funnel shape 304 when being used.

In use, medicament can be introduced into the port to the gauze portion 104, after which the port can be removed (such as being torn off of the second surface 116) or folded and adhered back to the second surface 116 until a subsequent use. The medicament can be applied to the port and then pressure applied to the port 322 to force the medicament into the gauze portion 104 or the medicament can simply flow into the gauze portion 106 from the port 302. As discussed above with regard to the second embodiment, the port 302 of the third embodiment can be used together with the first embodiment such that the medicament can be applied each time a new exposed gauze portion 112a is pulled to the first opening 110a.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. An adhesive bandage comprising:
a body portion having two or more gauze portions and an adhesive portion;
the adhesive portion having an adhesive on a first surface of the body portion adapted to adhere to skin; and
the body portion having a cavity for storing two or more gauze portions, the cavity having a first opening on the first surface for exposing one of the two or more gauze portions to the skin and a second opening on a second surface for removing the exposed gauze portion through the second opening and replacing the exposed gauze portion with another of the two or more gauze portions in the first opening;
wherein the two or more gauze portions are each separated by a separation portion allowing the exposed gauzed portion removed through the second opening to be separated from another of the two or more gauze portions.

2. The adhesive bandage of claim 1, wherein the separated portion is a weakened portion which is torn more easily than the gauze portion is torn.

3. The adhesive bandage of claim 1, wherein the separated portion corresponding to the exposed gauze portion is exposed through the second opening such that it can be pulled to remove the exposed gauze portion through the second opening and pull a subsequent one of the two or more gauze portions into the first opening.

4. The adhesive bandage of claim 1, wherein the second opening is a slit.

5. A method for changing a first gauze portion associated with an adhesive bandage, the method comprising:
adhering the adhesive bandage to a skin of a patient with the first gauze portion corresponding to a injured portion of the skin;
subsequent to the adhering, removing the first gauze portion; and
replacing the first gauze portion with a second gauze portion over the injured portion of the skin while the adhesive bandage remains adhered to the skin.

6. The method of claim 5, wherein the removing comprises pulling the first gauze portion through an opening on the adhesive bandage.

7. The method of claim 6, wherein the replacing comprises attaching the first gauze portion to the second gauze portion such that pulling the first gauze portion through the opening causes the second gauze portion to be positioned over the injured portion of the skin.

8. An adhesive bandage comprising:
a body portion having a gauze portion and an adhesive portion;
the adhesive portion having an adhesive on a first surface of the body portion adapted to adhere to skin; and
the body portion having a port in communication with the gauze portion for introducing a medicament to the gauze portion;
wherein the port is disposed on a second surface opposite to the first surface having the adhesive and the port is collapsible onto the second surface.

9. The adhesive bandage of claim 8, wherein the port is adhered to the second surface when in a collapsed state.

10. The adhesive bandage of claim 8, wherein the body portion has a cavity for storing two or more gauze portions, the cavity has a first opening on the first surface for exposing one of the two or more gauze portions to the skin and a second opening on a second surface for removing the exposed gauze portion through the second opening and replacing the exposed gauze portion with another of the two or more gauze portions in the first opening.

11. An adhesive bandage comprising:
a body portion having two or more gauze portions and an adhesive portion;
the adhesive portion having an adhesive on a first surface of the body portion adapted to adhere to skin; and
the body portion having a cavity for storing the two or more gauze portions, the cavity having a first opening on the first surface for exposing one of the two or more gauze portions to the skin and a second opening on a second surface for removing the exposed gauze portion through the second opening and replacing the exposed gauze portion with another of the two or more gauze portions in the first opening;
wherein the cavity has a first portion and a second portion, the first portion having the first opening for storing the exposed gauze portion and the second portion for storing the other of the two or more gauze portions.

12. The adhesive bandage of claim 11, wherein the second opening is a slit.

13. An adhesive bandage comprising:
a body portion having a gauze portion and an adhesive portion;
the adhesive portion having an adhesive on a first surface of the body portion adapted to adhere to skin; and
the body portion having a port in communication with the gauze portion for introducing a medicament to the gauze portion;
wherein the port is foldable into a shape having a reduced surface area when not being used.

14. The adhesive bandage of claim 13, wherein the port is unfoldable into a funnel shape when being used.

15. An adhesive bandage comprising:
a body portion having a gauze portion and an adhesive portion;
the adhesive portion having an adhesive on a first surface of the body portion adapted to adhere to skin; and
the body portion having a cavity for storing two or more gauze portions, the cavity having a first opening on the first surface for exposing one of the two or more gauze portions to the skin and a second opening on a second surface for removing the exposed gauze portion through the second opening and replacing the exposed gauze portion with another of the two or more gauze portions in the first opening;

wherein the second opening is a slit.

16. An adhesive bandage comprising:

a body portion having a gauze portion and an adhesive portion;

the adhesive portion having an adhesive on a surface of the body portion adapted to adhere to skin; and the body portion having at least one cavity for storing a medicament, the at least one cavity having an opening in communication with the gauze portion such that an application of pressure to the at least one cavity causes the medicament to flow into the gauze portion;

wherein the body portion has a cavity for storing two or more gauze portions, the cavity has a first opening on the first surface for exposing one of the two or more gauze portions to the skin and a second opening on a second surface for removing the exposed gauze portion through the second opening and replacing the exposed gauze portion with another of the two or more gauze portions in the first opening.

* * * * *